(12) United States Patent
Narayana et al.

(10) Patent No.: US 8,179,525 B2
(45) Date of Patent: May 15, 2012

(54) MIRROR MOUNTED INSIDE FILTER BLOCK OF A FLUORESCENCE MICROSCOPE TO PERFORM SERS AND METHOD THEREOF

(75) Inventors: Chandrabhas Narayana, Karnataka (IN); Gopalapura Venkataramu Pavan Kumar, Karnataka (IN)

(73) Assignee: Jawaharial Nehru Centre for Advanced Scientific Research, Bangalore, Karnataka (IN)

(*) Notice: Subject to any disclaimer, the term of this patent is extended or adjusted under 35 U.S.C. 154(b) by 324 days.

(21) Appl. No.: 12/203,185

(22) Filed: Sep. 3, 2008

(65) Prior Publication Data
US 2009/0244534 A1  Oct. 1, 2009

(30) Foreign Application Priority Data
Mar. 31, 2008  (IN) .............................. 787/CHE/2008

(51) Int. Cl.
*G01J 3/44*  (2006.01)

(52) U.S. Cl. ...................................................... 356/301
(58) Field of Classification Search ................. 356/300, 356/301, 72–73
See application file for complete search history.

(56) References Cited

U.S. PATENT DOCUMENTS

| | | | |
|---|---|---|---|
| 6,169,289 B1* | 1/2001 | White et al. | 250/458.1 |
| 2006/0034729 A1* | 2/2006 | Poponin | 422/82.05 |
| 2006/0134714 A1* | 6/2006 | Sundararajan et al. | 435/15 |
| 2006/0146323 A1* | 7/2006 | Bratkovski et al. | 356/301 |
| 2006/0290924 A1* | 12/2006 | Iketaki et al. | 356/300 |
| 2007/0177272 A1* | 8/2007 | Benson et al. | 359/584 |

* cited by examiner

*Primary Examiner* — Tarifur Chowdhury
*Assistant Examiner* — Abdullahi Nur
(74) *Attorney, Agent, or Firm* — Harness, Dickey & Pierce, PLC

(57) ABSTRACT

The present invention relates to spectroscopy, more particularly relates to a mirror made of glass plate and is coated with dielectric material, which is mounted inside filter block of fluorescence microscope to perform Surface Enhanced Raman Spectroscopy [SERS].

2 Claims, 5 Drawing Sheets

MIRROR MOUNTED INSIDE FILTER BLOCK OF A FLUORESCENCE MICROSCOPE TO PERFORM SERS AND METHOD THEREOF

FIELD

The present disclosure relates to spectroscopy, more particularly relates to a mirror which is adopted in a microscope to perform Surface Enhanced Raman Spectroscopy [SERS].

BACKGROUND

Ever since the Raman Effect was discovered, it has played a significant role in the field of vibrational spectroscopy. Although Raman scattering acts as an effective tool to probe molecular structure, it has some disadvantages like fluorescence overlap, small cross-sections and low sensitivity. Of late, due to the emergence of nanotechnology and improvement in sensitivity of optical instruments, Surface Enhanced Raman Scattering (SERS) has played an important role in overcoming the above-mentioned disadvantages. In this phenomenon, the Raman mode intensity of a molecule is enhanced by several orders of magnitude ($\sim 10^6$ to $10^{14}$) upon adsorption of the molecule to noble metal surfaces, which exhibit atomic scale roughness. Ever since its discovery, SERS has been utilized as an effective analytical tool to study molecules of biological interest and detection tool to probe different aspects of biology. Most importantly, it has been used to study protein-drug interaction and DNA complexes with a fair amount of success. SERS is used to unveil structural information of proteins, such as p300, which are not accessible to crystallographic techniques. SERS is equipped with a high degree of sensitivity to detect single molecules within a confined volume. One of the most important aspects of the SERS study is the experimental setup used to probe and detect the analyte under supervision. Although commercial Raman microscopes have played a key role in the success of SERS, most of them are expensive, sophisticated and lack flexibility. There have been a few successful attempts to build Raman microscopes previously, but most of them require specialized knowledge for construction. Therefore, it is important to design SERS set-up which is not only inexpensive, but also versatile to perform multiple experiments. Here in the instant invention setting up of SERS spectrometer using a simple viewing microscope with an epifluorescence attachment along with a mirror.

The fluorescence microscopes used in SERS are provided with dichroic mirror-cube holders. For fluorescence measurements a dichroic mirror is used, which is selected based on the excitation and emission band of the chromophore. In the case of Raman spectroscopy, this effectively blocks a large region of the Raman spectrum ($\sim 200$ cm$^{-1}$) close to the Rayleigh scattering. There is an added disadvantage of using the dichroic mirror as it also cutoff the high-frequency Raman spectra. The instant invention of mirror overcomes the problem faced by dichroic mirrors, wherein the dichroic mirrors of the fluorescence microscope are replaced with a special mirror.

SUMMARY

Accordingly, the invention provides for a mirror mounted inside filter block of a fluorescence microscope to perform Surface Enhanced Raman Spectroscopy (SERS), said mirror is made of glass plate and is coated with a dielectric material, wherein said dielectric material is silver and the coating is made at center of the glass plate with diameter ranging from about 2 mm to 3 mm and with an accuracy of about 0.1 mm.

Further, in another aspect, the disclosure provides a method of manufacturing a mirror for mounting inside filter block of a fluorescence microscope to perform Surface Enhanced Raman Spectroscopy (SERS) comprises acts of: designing a glass plate of the mirror according to dimensions of light tube of the fluorescence microscope; and coating of the glass plate with a dielectric material to obtain the mirror, wherein said dielectric material is silver and the coating is made at center of the glass plate with a diameter ranging from about 2 mm to 3 mm and with an accuracy of about 0.1 mm.

DRAWINGS

DETAILED DESCRIPTION

Figure 1:
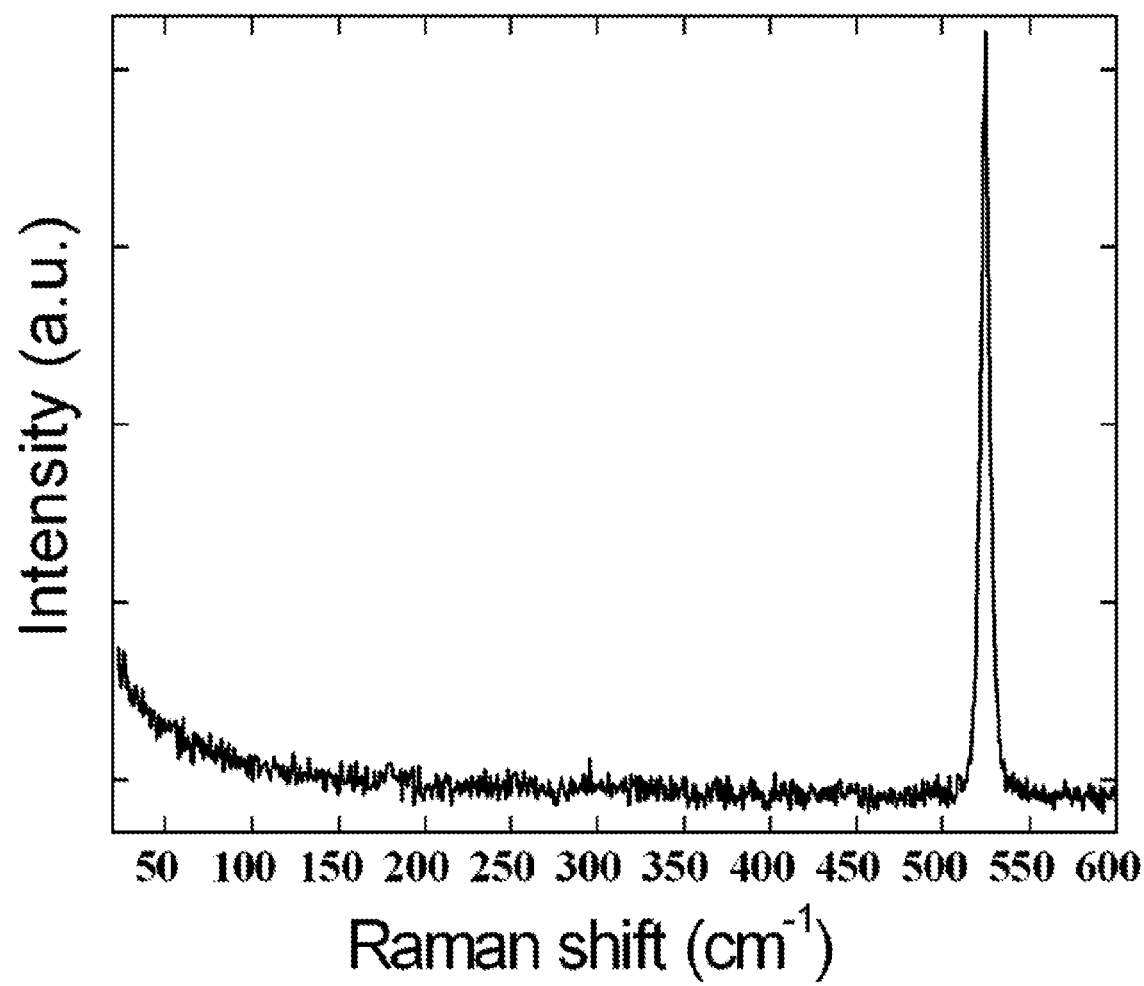
FIG. 1 shows Raman Spectra of silicon recorded in range 20-600 cm$^{-1}$.

The present invention is in relation to a mirror mounted inside filter block of fluorescence microscope to perform Surface Enhanced Raman Spectroscopy (SERS).

In yet another embodiment of the present invention the mirror is a glass plate coated with dielectric material.

In still another embodiment of the present invention the glass plate has thickness of about 1 mm, length of about 37.5 mm and breadth of about 25.4 mm, with workable range of +/−0.1 mm.

In still another embodiment of the present invention the dielectric coating is made at center of the glass plate with diameter ranging from about 2 mm to about 3 mm.

In still another embodiment of the present invention the mirror has reflectivity of about 99% in visible region of light ranging from about 400 nm to about 700 nm.

In still another embodiment of the present invention the dielectric coating is silver coating and is coated with an accuracy of about 0.1 mm.

In still another embodiment of the present invention the mirror is inclined at about 45° to reflect incident laser light from a source onto an analyte.

The present invention is in relation to a fluorescence microscope mounted with a mirror at filter block of the microscope to perform Surface Enhanced Raman Spectroscopy.

In still another embodiment of the present invention the microscope measures laser wavelength of about 50 cm$^{-1}$.

In still another embodiment of the present invention the microscope is used for wavelength of laser excitation in visible region.

In still another embodiment of the present invention the microscope is used in monitoring samples inside furnace, monitoring samples inside glove box, monitoring samples inside cell culture rooms and fume hoods to record Raman spectra and to perform SERS.

The present invention is in relation to a method of manufacturing a mirror mounted inside filter block of fluorescence microscope to perform Surface Enhanced Raman Spectroscopy (SERS) comprises acts of: designing glass plate of the mirror according to dimensions of light tube of the microscope; and coating of the glass plate with silver to obtain the adapted mirror.

In still another embodiment of the present invention the silver coating is made at center of the glass plate with diameter ranging from about 2 mm to about 3 mm.

In still another embodiment of the present invention the mirror is inclined at about 45° to reflect incident laser light onto an analyte.

The present invention is in relation to a method to perform Surface Enhanced Raman Spectroscopy (SERS) using a mirror mounted inside filter block of fluorescence microscope comprises acts of: preparing analyte sample by mixing the analyte with silver nano-particles; depositing the analyte sample over a glass slide; placing the deposited glass slide on stage of the microscope; passing laser light beams from source onto the mirror; and recording spectral rays using detector.

In still another embodiment of the present invention the mixing of analyte with silver nano-particles is in the ratio of about 5:95 by volume and broad workable range is 1:15 to 1:20.

In still another embodiment of the present invention the recording of spectral rays to perform SERS takes time ranging from 1-30 seconds.

In still another embodiment of the present invention the laser source is Helium-Neon (He—Ne) and or Nd-YAG laser.

The mirror is usable in any microscope as it sits in the position of the dichroic mirror in the light tube of the microscope. This is achieved by designing the mirror with the exact dimensions of the dichroic mirror. The microscopes is used in extreme situations such as monitoring samples inside a furnace, monitoring samples inside a glove box, monitoring samples inside cell culture rooms, fume hoods etc. A normal Raman spectrometer cannot go into these places, since a microscope can be placed in these places, the instant invention is used to record Raman spectra and SERS from the samples in this environment without bring out the samples.

The instant invention facilitates in going closer to the Laser wavelength (~50 cm$^{-1}$), Usual dichroic mirrors used have a very high cut off close to the excitation wavelength as well as are not broad band transmission. Since the instant do not use any filters, there is no cut off and no need to replace these for any wavelength of light like done in the case of dichroic mirrors. Hence they are usable in any wavelength of laser light in the range 400 nm to 900 nm without loss of signal. The 50 cm$^{-1}$ cut off is also coming due to the edge filter used. The salient feature of the instant invention is that it doesn't have any cut off for the Raman signal, and it is used for any wavelength of laser excitation in the visible region without loss of signal.

For the present work, a Nikon Eclipse 50i (Nikon, Japan) microscope with an epi-fluorescent attachment as the main part of the collection optics for the Raman spectrometer is selected. Other fluorescence microscope is used for the same purpose. The epi-fluorescent attachment, which is used for fluorescent imaging, contains the bayonet mount for placing the white light source. The laser of desired wavelength is launched through this mount. An aluminum disc with 1 mm hole in the centre, sitting snugly on the epi-fluorescent lamp attachment, helps in aligning the laser beam along the optical axis. The adjustable field diaphragm present in the microscope, which restricts white light illumination on the area of the specimen being viewed, was used as the second aperture to assist the alignment of the laser beam along the optical axis. The diaphragm is used to focus the laser beam onto the sample under observation. The mirror has an Ag coating of 2 mm diameter at the centre of a 25.2×35.6 (±0.2) mm fused silica substrate of 1.1 mm thickness. The mirror has a reflection band between 400 and 900 nm, with reflectivity greater than 99%. With this modification, low-frequency Raman spectrum up to ~50 cm$^{-1}$ is recorded, as shown in the case of silicon in FIG. 1. The diameter of the laser beam was ~1 mm, which was completely reflected by the mirror of 2 mm diameter.

The microscope is equipped with an additional camera port, which is used for imaging the field-of-view. A digital camera is mounted on this port. A 200 mm multimode single core optical fibre with a band-pass of 400-1000 nm is used to collect the scattered light. The length of the optical fibre is between 1.5 and 5 m. In order to optimize the collection of the scattered light into the fibre, a microscope objective is used at the camera port of the trinocular of the microscope.

Figure 2:
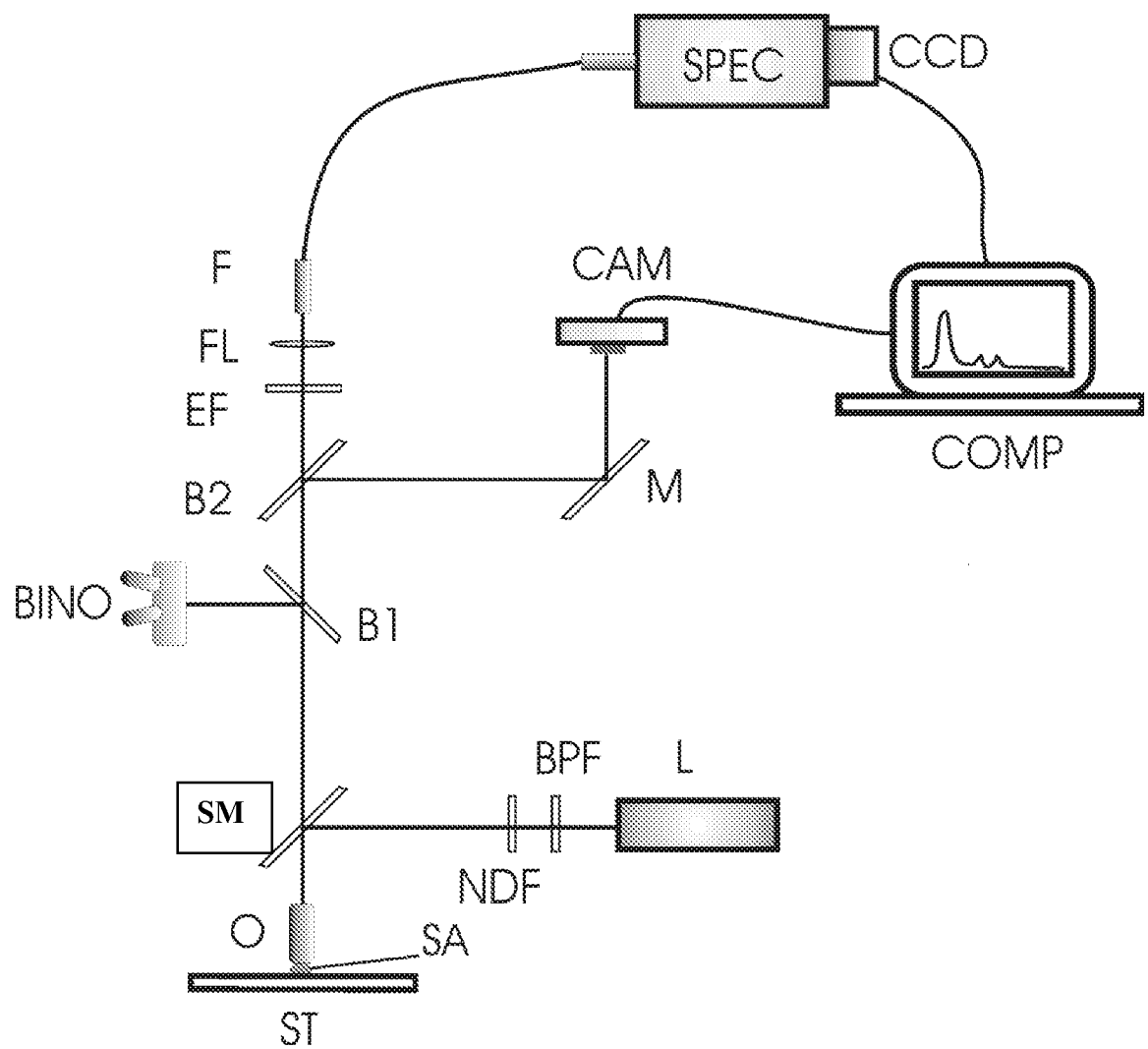
FIG. 2 shows schematic of the micro-Raman system built with a simple viewing microscope.

FIG. 2 shows the schematic of the micro-Raman system built with a simple viewing microscope with an epifluorescent attachment .ST, stage; SA, Sample; O, objective lens; L, Laser; BPF, Band Pass Filter; NDF, Neutral density filter; SM, Special mirror; B1, B2, Beam Splitters; M, mirror; BINO, Binocular; EF, edge filter; FL, focusing lens; F optical fibre; SPEC, Spectrometer; CCD, Charged coupled device; COMP, computer; CAM, camera. The Raman excitation light (532 nm) provided by a solid-state frequency-doubled Nd-YAG laser (Model G-SLM-015, Suwtech Inc., China), which traversed a band-pass filter (LL01-532-12.5, Semrock, UK), used as the excitation source. The 632.8 nm laser source from a He—Ne laser (Model No. 30994, Newport, USA) with appropriate band-pass filter (LL01-633-12.5, Semrock) also used in some of the experiments. In order to reflect the laser beam by 45° onto the sample, a special mirror is used. The scattered light passes through an edge filter (LP03-532RS-25, Semrock) placed at the output camera port of the trinocular. The scattered light is focused onto the optical fibre using an objective lens with a numerical aperture (NA) of 0.4-0.5, as shown in the FIG. 2. The other end of the optical fibre is f-number matched at the factory to a 0.55 m spectrograph (Jobin-Yovn 550 Triax, Instruments SA, Inc., NJ, USA) attached with a liquid nitrogen-cooled CCD detector. The f-number matching is achieved using a couple of achromatic doublet lens with appropriate focal lengths and the clear apertures.

The spectrograph itself has a computer-controlled adjustable slit and a turret which holds three gratings for a range of measurements. For the present Raman studies, a 600 grooves mm$^{-1}$ grating is used along with the 200 mm spectrograph entrance slit setting, providing ~5 cm−1 resolution. A digital camera (Nikon Coolpix 5400, Nikon, Japan) atop the microscope allowed for registration of the focused laser spot and focusing the image of the laser spot onto the optical fibre (by back-illuminating the optical fibre). Typically, for Raman studies on liquid samples, a 60× infinity-corrected water-immersion objective (Nikon Fluor, NA 1.00, Nikon, Japan) is used. The laser power is ~8 mW at the sample. For SERS measurements citrate-reduced Ag nano-particles is used and prepared using the standard Lee and Meisel method. The analyte of interest is mixed with the Ag nano-particles in the ratio of 5:95 by volume and deposited over a glass slide before bringing the water-immersion objective in contact with it for measurements. The final concentration of the analyte was 1 mM. The spectral accumulation time is typically 1-30 s for all measurements.

Performance of the Constructed Microscope

Figure 3:
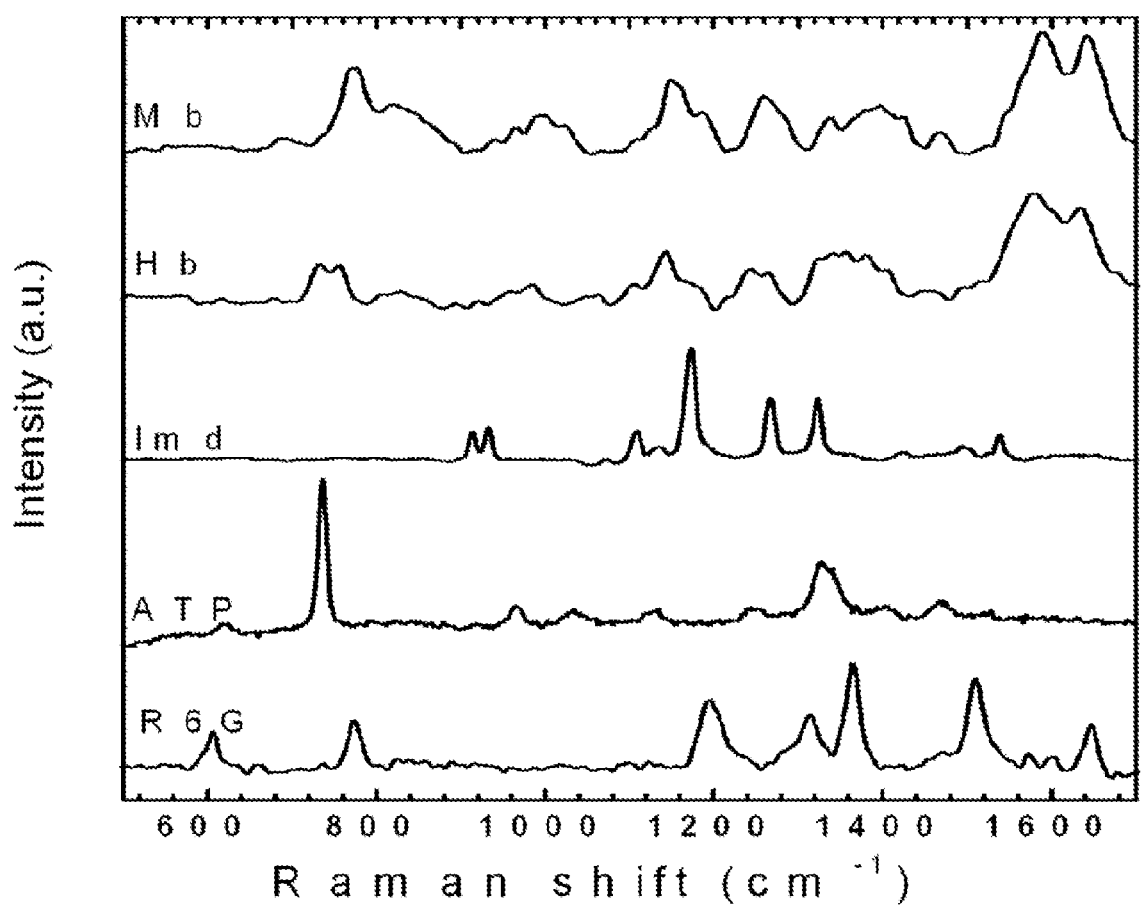
FIG. 3 shows SERS spectra of (a) rhodamine 6G (R6G), (b) imidazole (Imd), (c) adenosine triphosphate (ATP), (d) haemoglobin (Hb) and (e) myoglobin (Mb).
Figure 4:
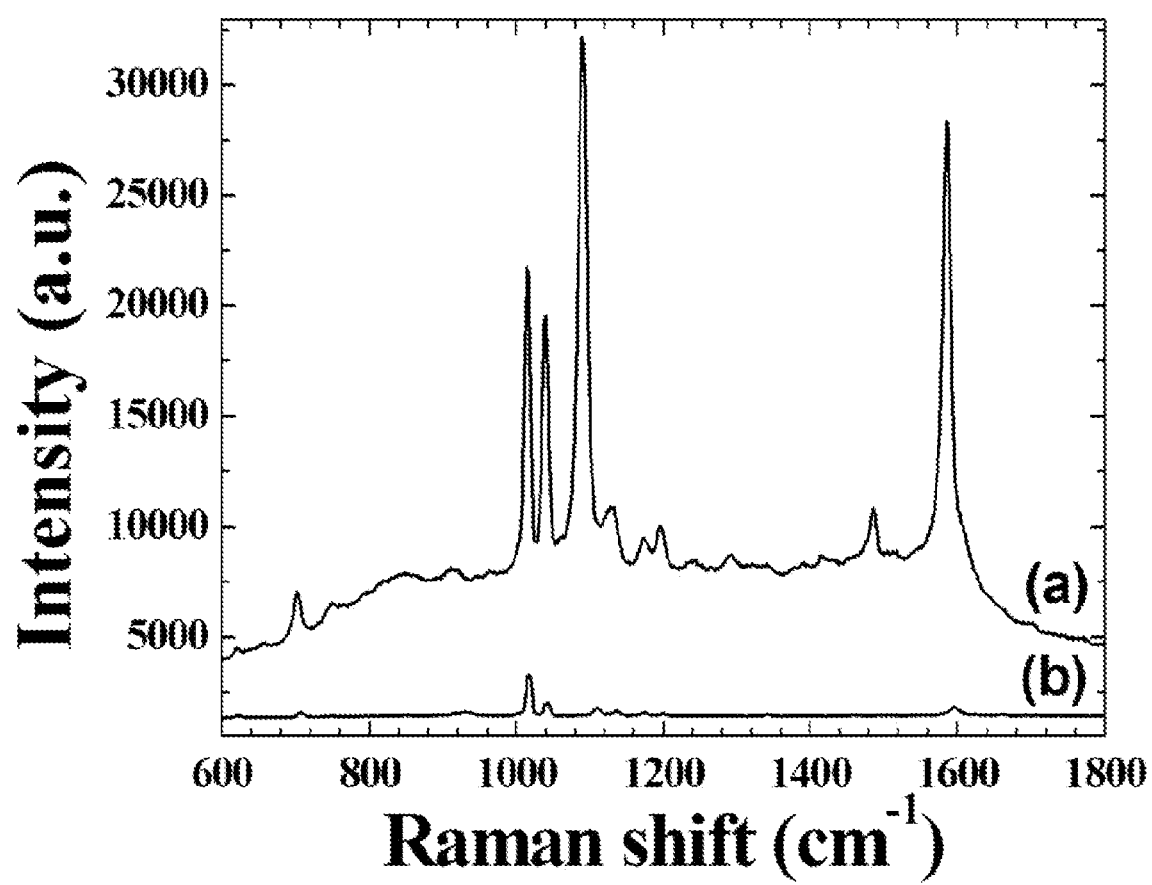
FIG. 4 shows Raman (a) and SERS (b) spectra of thiophenol.

In order to demonstrate that the micro-Raman instrument constructed by the above method used to detect small traces of biologically important molecules are performed by SERS on a variety of molecules like imidazole (a small organic molecule), rhodamine 6G (dye molecule), adenosine triphosphate and macromolecules such as haemoglobin and myoglobin at micromolar concentrations. FIG. 3 shows the SERS spectra of these molecules with a typical integration time of 1-30 s. All the spectra obtained are in good agreement with previous reported results. The typical volume of the nano-particle analyte system used for such detection is 30 ml. It is found that 7 ml is the minimum volume of the composite which produced detectable Raman spectra. Here, all these molecules are detected at nano-Molar concentrations with this set-up using different sample preparation techniques and excitation sources. Also, the sensitivity of detection is increased by adding a small concentration of NaCl solution, which acts as an aggregating agent for the Ag nano-particles. In order to quantify the SERS enhancement, a neat solution of thiophenol is used for recording the Raman spectra, and a 1 mM solution is used for SERS measurements. FIGS. 4 (a) and (b) shows the Raman and SERS spectra of thiophenol (TP). The Raman enhancement factor (or gain), is calculated for the 1080 $cm^{-1}$ band of TP using the standard method, and found to be of the order $10^6$. Other molecules, such as nucleic acid bases, different dye molecules, proteins and small molecules were detected at low concentrations using this instrument.

Role and Usage of Water Immersion Objective in SERS

Figure 5:
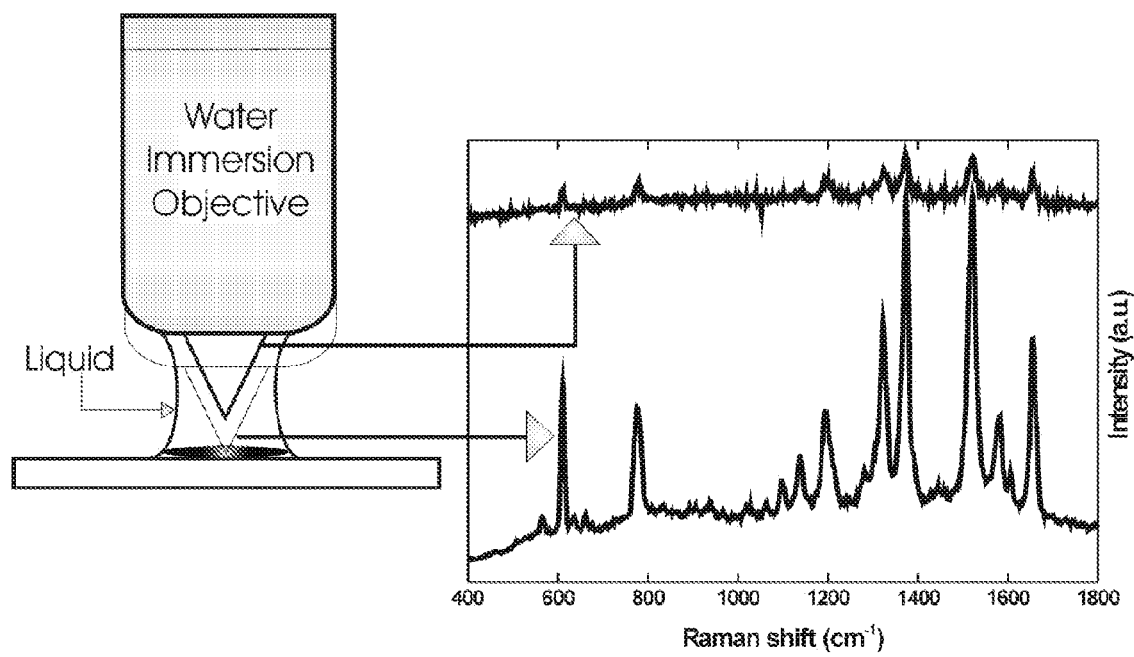
FIG. 5 is a schematic of the water-immersion objective lens focused at two different spots on the glass slide with the analyte-nano-particle composite solution used for SERS measurements.

One of the most important aspects of the Raman instrumentation for SERS studies on bio-molecules is the ability to perform experiments in aqueous phase for which one uses a water-immersion objective lens. In order to obtain high spatial resolution, high throughput, and tight focusing of the incident beam in SERS studies, it is necessary to use a high NA and a high magnification objective lens, like the 1.2 NA and 60× magnification lens used in the present experiment. This has been a common approach for single-molecule SERS experiments as well as confocal Raman imaging. Through a simple experiment, in the instant invention, the ability to spatially resolve two regions inside the aqueous solution along the focusing direction, which are separated by only a few micrometers. This reveals two important aspects, namely, ability to probe a very small volume, and a limited confocal imaging ability. FIG. 5 shows the schematic of the objective lens focusing at two different heights inside the liquid, which formed a drop over the glass slide. The SERS spectra recorded on these two spots are also shown alongside. R6G with Ag nano-particles acts as a good test sample since it gives a strong SERS signal. The two spots selected were separated by about a few micrometers; one of them was on the glass-liquid interface and the other was within the liquid just above it. It is interesting to note that the intensity of the strongest mode of R6G (1373 $cm^{-1}$) increases by a factor of 7.5 in the case of the glass-liquid interface compared to the one within the liquid. The R6G-nano-particle composite in the liquid is under constant Brownian motion and therefore, the Raman signal collected for a stipulated time is a resultant of a time-averaged signal of the composite residing in the probed volume of the laser beam. At the glass-liquid interface, there is an aggregation of the R6G-nano-particle composite due to sedimentation with time. These stationary composite particles hence provides large Raman signal due to increase in the Raman scattering probability. This behavior is common to all the molecules studied using SERS, and hence it is an important tip for SERS experiments.

In present invention, a simple viewing microscope is used for fluorescence imaging is modified to perform SERS experiments with the functionality of a commercial Raman setup. One can detect a small trace of important biological molecules using the set-up. Using this instrument, it is able to detect several biologically relevant proteins, and have provided structural information during small molecule-protein interactions.

What is claimed is:

1. A mirror mounted inside filter block of a fluorescence microscope to perform Surface Enhanced Raman Spectroscopy (SERS), said mirror is made of a glass plate and is partially coated with a dielectric material, wherein said dielectric material is silver and the coating is made at center of the glass plate with diameter ranging from about 2 mm to about 3 mm and with an accuracy of about 0.1 mm.

2. A method of manufacturing a mirror for mounting inside filter block of a fluorescence microscope to perform Surface Enhanced Raman Spectroscopy (SERS) comprises acts of:
   a. designing a glass plate of the mirror according to dimensions of light tube of the fluorescence microscope; and
   b. partially coating the glass plate with a dielectric material to obtain the mirror, wherein said dielectric material is silver and the coating is made at center of the glass plate with diameter ranging from about 2 mm to about 0.3 mm and with an accuracy of about 0.1 mm.

* * * * *